United States Patent
Hon

(10) Patent No.: US 10,588,353 B2
(45) Date of Patent: Mar. 17, 2020

(54) ELECTRONIC CIGARETTE

(71) Applicant: FONTEM HOLDINGS 1 B.V., Amsterdam (NL)

(72) Inventor: Lik Hon, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 0 days.

(21) Appl. No.: 15/902,712

(22) Filed: Feb. 22, 2018

(65) Prior Publication Data

US 2018/0184719 A1 Jul. 5, 2018

Related U.S. Application Data

(63) Continuation of application No. 15/091,017, filed on Apr. 5, 2016, now Pat. No. 10,383,366, which is a
(Continued)

(30) Foreign Application Priority Data

Feb. 11, 2009 (CN) ..................... 2009 2 0001296 U

(51) Int. Cl.
*A24F 47/00* (2020.01)
*H05B 3/00* (2006.01)
(Continued)

(52) U.S. Cl.
CPC ......... *A24F 47/008* (2013.01); *A61M 11/041* (2013.01); *A61M 11/042* (2014.02);
(Continued)

(58) Field of Classification Search
None
See application file for complete search history.

(56) References Cited

U.S. PATENT DOCUMENTS

| 3,200,819 A | 8/1965 | Gilbert |
| 4,735,217 A | 4/1988 | Gerth et al. |

(Continued)

FOREIGN PATENT DOCUMENTS

| CN | 1233436 A | 11/1999 |
| CN | 2719043 Y | 8/2005 |

(Continued)

OTHER PUBLICATIONS

IP Office Korea, Application No. KR10-2017-7036784, Last Preliminary Rejection with English Translation, dated Oct. 30, 2018.
(Continued)

*Primary Examiner* — Phu H Nguyen
(74) *Attorney, Agent, or Firm* — Perkins Coie LLP; Kenneth H. Ohriner

(57) ABSTRACT

An atomizing electronic cigarette has an atomizing core component and a liquid storage component, including an electric heater. The electric heater may have a through hole aligned with a channel passing through the liquid storage component. The cigarette can heat and uniformly vaporize liquid from the liquid storage component, with the user inhaling the vaporized liquid. The vapor generated by the atomizing process may be cooled as it flows through the channel.

25 Claims, 2 Drawing Sheets

Related U.S. Application Data continuation of application No. 14/307,663, filed on Jun. 18, 2014, now Pat. No. 9,320,300, which is a continuation of application No. 13/208,257, filed on Aug. 11, 2011, now abandoned, which is a continuation of application No. PCT/CN2010/000125, filed on Jan. 28, 2010.

(51) Int. Cl.
  *A61M 11/04* (2006.01)
  *A61M 15/06* (2006.01)
  *H05B 3/06* (2006.01)
  *A61M 16/00* (2006.01)

(52) U.S. Cl.
  CPC ........... *A61M 15/06* (2013.01); *H05B 3/0014* (2013.01); *H05B 3/06* (2013.01); *A61M 2016/0024* (2013.01); *A61M 2205/8206* (2013.01)

(56) References Cited

U.S. PATENT DOCUMENTS

| | | | |
|---|---|---|---|
| 4,947,874 | A | 8/1990 | Brooks |
| 4,947,875 | A | 8/1990 | Brooks |
| 4,981,522 | A | 1/1991 | Nichols et al. |
| 5,095,921 | A | 3/1992 | Morris |
| 5,101,838 | A | 4/1992 | Schwartz et al. |
| 5,144,962 | A | 9/1992 | Morris |
| 8,511,318 | B2 | 8/2013 | Hon |
| 2004/0089314 | A1 | 5/2004 | Felter et al. |
| 2005/0016550 | A1 | 1/2005 | Katase |
| 2006/0016453 | A1 | 1/2006 | Kim |
| 2006/0196518 | A1 | 9/2006 | Hon |
| 2008/0092912 | A1 | 4/2008 | Robinson |
| 2009/0095311 | A1* | 4/2009 | Han ................. A24F 47/008 131/194 |
| 2009/0126745 | A1* | 5/2009 | Hon ................. A24F 47/008 131/273 |
| 2009/0188490 | A1 | 7/2009 | Han |
| 2009/0272379 | A1 | 11/2009 | Thorens et al. |
| 2011/0011396 | A1 | 1/2011 | Fang |

FOREIGN PATENT DOCUMENTS

| | | |
|---|---|---|
| CN | 2887086 Y | 4/2007 |
| CN | 200966824 Y | 10/2007 |
| CN | 101077225 A | 11/2007 |
| CN | 200997909 Y | 1/2008 |
| CN | 101116542 A | 2/2008 |
| CN | 201018927 Y * | 2/2008 |
| CN | 201018927 Y | 2/2008 |
| CN | 201054977 Y | 5/2008 |
| CN | 201085044 Y | 7/2008 |
| CN | 201379072 Y | 1/2010 |
| DE | 102006004484 A1 | 8/2007 |
| EP | 0845220 A1 | 6/1997 |
| EP | 0893071 A1 | 7/1998 |
| EP | 1736065 A1 | 3/2005 |
| EP | 1891867 A2 | 2/2008 |
| JP | H03-232481 A | 10/1991 |
| JP | 2016-073316 A | 12/2016 |
| WO | 1998023171 A1 | 6/1998 |
| WO | 2004089126 A1 | 10/2004 |
| WO | 2007078273 A1 | 7/2007 |
| WO | 2007131449 A1 | 11/2007 |
| WO | 2000028843 | 7/2015 |

OTHER PUBLICATIONS

EPO, Application No. 10740882.5, Patent No. 2404515B, Decision Revoking the Patent, dated May 3, 2018.
Anonymous, Application No. 14155504.5, Third Party Observations, Apr. 18, 2018.
Certified English Translation of priority document CN200920001296U, Mar. 25, 2010.
EPO, Application No. 10740882.5, Annex to the summons to oral proceedings, Jun. 20, 2017.
EPO, Application No. 14155504.5, Exam Report, dated Apr. 12, 2018.
Japanese Patent Office, Application No. 2017-093905, Notice of Rejection, dated Jul. 19, 2018.
USPTO, U.S. Appl. No. 15/466,753, Nonfinal Office Action, dated Sep. 7, 2018.
USPTO, U.S. Appl. No. 15/091,017, Nonfinal Office Action, dated Sep. 14, 2018.
IP Office China PRC, CN201080016105.6, Fourth Office Action with English Translation, dated Sep. 12, 2014.
IP Office Japan, Application No. JP2017-093905, Notice of Rejection with English Translation, dated Mar. 19, 2019.
USPTO, U.S. Appl. No. 13/426,817, Interview Summary, dated Sep. 27, 2013.
Uspto, U.S. Appl. No. 13/426,817, Notice of Allowance, dated Dec. 23, 2013.
Uspto, U.S. Appl. No. 14/307,663, Notice of Allowance, dated Mar. 2, 2015.
USPTO, U.S. Appl. No. 15/091,017, Advisory Action, dated Feb. 26, 2018.
USPTO, U.S. Appl. No. 15/091,017, Interview Summary, dated Nov. 30, 2018.
USPTO, U.S. Appl. No. 15/091,017, Notice of Allowance, dated Mar. 29, 2019.
USPTO, U.S. Appl. No. 15/466,753, Interview Summary, dated Nov. 30, 2018.
USPTO, U.S. Appl. No. 15/466,753, Final Office Action, dated Feb. 21, 2019.
IP Office Korea, Application No. KR10-2017-7036784, KIPO's Notice of Final Rejection with English Translation, dated May 27, 2019.
Bejing Intellectual Property Court, People'S Republic of China, Administrative Judgment regarding Chinese Patent No. 201080016105.6 with English Translation, Jun. 25, 2019.
IP Office Korea, Application No. KR10-2017-7036784, KIPO's Second Notice of Final Rejection with English Translation, dated Aug. 22, 2019.
Anonymous, Third Party Observation for EP20100740882, Oct. 3, 2013.
Anonymous, Third Party Observation for EP20100740882, Apr. 17, 2014.
CB Distributors, Inc. and DR Distributors, LLC, Petition for Inter Partes Review of U.S. Pat. No. 8,689,805—IPR2015-01529, Sep. 22, 2014.
CB Distributors, Inc. and DR Distributors, LLC, Petition for Inter Partes Review of U.S. Pat. No. 8,689,805—IPR2015-01529, Ex. 1001 U.S. Pat. No. 8,689,805 to Hon, Sep. 22, 2014.
CB Distributors, Inc. and DR Distributors, LLC, Petition for Inter Partes Review of U.S. Pat. No. 8,689,805—IPR2015-01529, Ex. 1002 Declaration of Samuel David Piper, P.E., Sep. 22, 2014.
CB Distributors, Inc. and DR Distributors, LLC, Petition for Inter Partes Review of U.S. Pat. No. 8,689,805—IPR2015-01529, Ex. 1003 Jan. 17, 2013, Office Action, dated Sep. 22, 2014.
CB Distributors, Inc. and DR Distributors, LLC, Petition for Inter Partes Review of U.S. Pat. No. 8,689,805—IPR2015-01529, Ex. 1004 China Patent Application No. CN200966824 Y to Hon, Sep. 22, 2014.
CB Distributors, Inc. and DR Distributors, LLC, Petition for Inter Partes Review of U.S. Pat. No. 8,689,805—IPR2015-01529, Ex. 1005 Certified English Translation of China Patent Application No. CN200966824Y to Hon, Sep. 22, 2014.
CB Distributors, Inc. and DR Distributors, LLC, Petition for Inter Partes Review of U.S. Pat. No. 8,689,805—IPR2015-01529, Ex. 1006 Feb. 15, 2013, Response to Office Action, dated Sep. 22, 2014.
CB Distributors, Inc. and DR Distributors, LLC, Petition for Inter Partes Review of U.S. Pat. No. 8,689,805—IPR2015-01529, Ex. 1007 Jun. 7, 2013, Final Office Action, dated Sep. 22, 2014.

(56) References Cited

OTHER PUBLICATIONS

CB Distributors, Inc. and DR Distributors, LLC, Petition for Inter Partes Review of U.S. Pat. No. 8,689,805—IPR2015-01529, Ex. 1008 Sep. 27, 2013, Interview Summary, dated Sep. 22, 2014.
CB Distributors, Inc. and DR Distributors, LLC, Petition for Inter Partes Review of U.S. Pat. No. 8,689,805—IPR2015-01529, Ex. 1009 Sep. 13, 2013, Response to Office Action, dated Sep. 22, 2014.
CB Distributors, Inc. and DR Distributors, LLC, Petition for Inter Partes Review of U.S. Pat. No. 8,689,805—IPR2015-01529, Ex. 1010 Sep. 13, 2013, Declaration of Lik Hon Under CFR Rule 1.132, Sep. 22, 2014.
CB Distributors, Inc. and DR Distributors, LLC, Petition for Inter Partes Review of U.S. Pat. No. 8,689,805—IPR2015-01529, Ex. 1011 U.S. Patent Application No. US 2009/0188490 to Hon ("Hon '490"), Sep. 22, 2014.
CB Distributors, Inc. and DR Distributors, LLC, Petition for Inter Partes Review of U.S. Pat. No. 8,689,805—IPR2015-01529, Ex. 1012 Dec. 23, 2013, Notice of Allowance and Examiner's Amendment, dated Sep. 22, 2014.
CB Distributors, Inc. and DR Distributors, LLC, Petition for Inter Partes Review of U.S. Pat. No. 8,689,805—IPR2015-01529, Ex. 1013 China Patent Application No. CN201018927Y to Wang, Sep. 22, 2014.
CB Distributors, Inc. and DR Distributors, LLC, Petition for Inter Partes Review of U.S. Pat. No. 8,689,805—IPR2015-01529, Ex. 1014 Certified English Translation of China Patent Application No. CN201018927 Y to Wang, Sep. 22, 2014.
CB Distributors, Inc. and DR Distributors, LLC, Petition for Inter Partes Review of U.S. Pat. No. 8,689,805—IPR2015-01529, Ex. 1015 WO 2007/131449 A1 to Hon, Sep. 22, 2014.
CB Distributors, Inc. and DR Distributors, LLC, Petition for Inter Partes Review of U.S. Pat. No. 8,689,805—IPR2015-01529, Ex. 1016 Certified English Translation of WO 2007/131449 A1 to Hon, Sep. 22, 2014.
CB Distributors, Inc. and DR Distributors, LLC, Petition for Inter Partes Review of U.S. Pat. No. 8,689,805—IPR2015-01529, Ex. 1017 U.S. Patent Application No. US 2006/0196518 to Hon, Sep. 22, 2014.
CB Distributors, Inc. and DR Distributors, LLC, Petition for Inter Partes Review of U.S. Pat. No. 8,689,805—IPR2015-01529, Ex. 1018 WO 2007/078273 A1 to Liu, Sep. 22, 2014.
Collins, John M., Expert Report—Invalidity (Excerpts), CV14-01645, Jun. 18, 2015.
Collins, John M., Expert Report—Invalidity, CV14-01645-Appendix I-1-'805, Jun. 18, 2015.
Collins, John M., Expert Report—Invalidity, CV14-01645-Appendix I-2-'805, Jun. 18, 2015.
Collins, John M., Expert Report—Invalidity, CV14-01645-Appendix I-3-'805, Jun. 18, 2015.
Collins, John M., Expert Report—Invalidity, CV14-01645-Appendix I-4-'805, Jun. 18, 2015.
Eisenfuhr Speiser Patentanwalte Rechtsanwalte Part GMBH, Opposition to European Patent 2404515 (application No. EP10740882.5), Jun. 17, 2016, 38 pgs.
Eurasian Patent Office, Official Action for EA201171031, dated Mar. 30, 2015.
Eurasian Patent Office, Official Action for EA201171031, dated Jul. 2, 2014.
Eurasian Patent Office, Official Action for EA201171031, dated Jul. 4, 2013.
Eurasian Patent Office, Search Report for EA201690438, dated Jan. 15, 2018.
Eurasian Patent Office, Search Report for Eurasian Patent Application No. 201690438, dated Jan. 15, 2018, 1 pg.
European Patent Office, Extended European Search Report for EP10740882.5, dated Oct. 8, 2013.
European Patent Office, Extended European Search Report for EP14155504.5, dated Jan. 30, 2015.
Fang Xiao, 1st Supplemental Petition for Invalidation of CN201080016105.6, with English Translation, Apr. 25, 2017.
Fang Xiao, 2nd Supplemental Petition for Invalidation of CN201080016105.6, with English Translation, Jun. 27, 2017.
Intellectual Property India, Application No. 6236/CHENP/2011, First Examination Report, dated May 29, 2018.
IP Australia, Patent Examination Report for AU2014206215, dated Jun. 6, 2016.
IP Australia, Patent Examination Report No. 1 for AU2010213270, dated Aug. 5, 2013.
Japanese Patent Office, Office Action for JP2011-549417, with English Translation, dated Jan. 17, 2014.
Japanese Patent Office, Office Action for JP2011-549417, with English Translation, dated Oct. 6, 2014.
Japanese Patent Office, Office Action for JP2011-549417, with English Translation, dated Jun. 24, 2015.
Joyetech Deutschland GMBH, Opposition to European Patent EP2404515 (application No. EP10740882.5), Jun. 17, 2016, 24 pgs.
Joyetech Deutschland GMBH, Response filed in Opposition of European Patent No. 2404515B1, Jan. 19, 2018, 26 pgs.
JT International S.A., Opposition to European Patent EP2404515 (application No. EP10740882.5), Sep. 10, 2015.
JT International S.A., Petition for Inter Partes Review of U.S. Pat. No. 8,689,805—1PR2015-01578, Jul. 15, 2015.
JT International S.A., Petition for Inter Partes Review of U.S. Pat. No. 8,689,805—IPR2015-01578, Ex. 1001 U.S. Pat. No. 8,689,805 to Hon, Jul. 15, 2015.
JT International S.A., Petition for Inter Partes Review of U.S. Pat. No. 8,689,805—IPR2015-01578, Ex. 1002 Declaration of Jeffrey A. Schuster, Ph.D., Jul. 15, 2015.
JT International S.A., Petition for Inter Partes Review of U.S. Pat. No. 8,689,805—IPR2015-01578, Ex. 1003 Jan. 17, 2013, Office Action, dated Jul. 15, 2015.
JT International S.A., Petition for Inter Partes Review of U.S. Pat. No. 8,689,805—IPR2015-01578, Ex. 1004 Feb. 15, 2013, Response to Non-Final Office Action, dated Jul. 15, 2015.
JT International S.A., Petition for Inter Partes Review of U.S. Pat. No. 8,689,805—IPR2015-01578, Ex. 1005 Jun. 7, 2013, Final Office Action, dated Jul. 15, 2015.
JT International S.A., Petition for Inter Partes Review of U.S. Pat. No. 8,689,805—IPR2015-01578, Ex. 1006 Sep. 13, 2013, Response to Final Office Action, dated Jul. 15, 2015.
JT International S.A., Petition for Inter Partes Review of U.S. Pat. No. 8,689,805—IPR2015-01578, Ex. 1007 Sep. 13, 2013, Declaration of Lik Hon Under CFR Rule 1.132, Jul. 15, 2015.
JT International S.A., Petition for Inter Partes Review of U.S. Pat. No. 8,689,805—IPR2015-01578, Ex. 1008 Sep. 27, 2013, Interview Summary, dated Jul. 15, 2015.
JT International S.A., Petition for Inter Partes Review of U.S. Pat. No. 8,689,805—IPR2015-01578, Ex. 1009 Dec. 23, 2013, Notice of Allowance and Examiner's Amendment, dated Jul. 15, 2015.
JT International S.A., Petition for Inter Partes Review of U.S. Pat. No. 8,689,805—IPR2015-01578, Ex. 1010 China Patent Application No. CN 200966824 Y to Hon, Jul. 15, 2015.
JT International S.A., Petition for Inter Partes Review of U.S. Pat. No. 8,689,805—IPR2015-01578, Ex. 1011 Certified English Translation of China Patent Application No. CN200966824 Y to Hon, Jul. 15, 2015.
JT International S.A., Petition for Inter Partes Review of U.S. Pat. No. 8,689,805—IPR2015-01578, Ex. 1012 U.S. Patent Application No. US 2009 0188490 to Hon, Jul. 15, 2015.
JT International S.A., Petition for Inter Partes Review of U.S. Pat. No. 8,689,805—IPR2015-01578, Ex. 1013 The American Heritage Dictionary ("conduct") ("permeate"), Jul. 15, 2015.
JT International S.A., Petition for Inter Partes Review of U.S. Pat. No. 8,689,805—IPR2015-01578, Ex. 1014 Merriam-Webster.com ("sleeve"), Jul. 15, 2015.
JT International S.A., Petition for Inter Partes Review of U.S. Pat. No. 8,689,805—IPR2015-01578, Ex. 1015 China Patent Application Publication No. 201085044 Y to Fang, Jul. 15, 2015.
JT International S.A., Petition for Inter Partes Review of U.S. Pat. No. 8,689,805—IPR2015-01578, Ex. 1016 Certified English Translation of China Patent Application Publication No. 2010085044 Y to Fang, Jul. 15, 2015.

(56) References Cited

OTHER PUBLICATIONS

JT International S.A., Petition for Inter Partes Review of U.S. Pat. No. 8,689,805—IPR2015-01578, Ex. 1017 China Patent Application No. CN 201018927 Y to Wang, Jul. 15, 2015.
JT International S.A., Petition for Inter Partes Review of U.S. Pat. No. 8,689,805—IPR2015-01578, Ex. 1018 Certified English Translation of China Patent Application No. CN 201018927 Y to Wang, Jul. 15, 2015.
JT International S.A., Petition for Inter Partes Review of U.S. Pat. No. 8,689,805—IPR2015-01578, Ex. 1019 WO 2007/131449 A1 to Hon, Jul. 15, 2015.
JT International S.A., Petition for Inter Partes Review of U.S. Pat. No. 8,689,805—IPR2015-01578, Ex. 1020 Certified English Translation of WO 2007/131449 AI to Hon, Jul. 15, 2015.
JT International S.A., Petition for Inter Partes Review of U.S. Pat. No. 8,689,805—IPR2015-01578, Ex. 1021 WO 00/28843 A1 to Pienemann, Jul. 15, 2015.
JT International S.A., Petition for Inter Partes Review of U.S. Pat. No. 8,689,805—IPR2015-01578, Ex. 1022 Certified English Translation of WO 00/28843 A1 to Pienemann, Jul. 15, 2015.
JT International S.A., Petition for Inter Partes Review of U.S. Pat. No. 8,689,805—IPR2015-01578, Ex. 1023 WO 2007/078273 AI to Liu, Jul. 15, 2015.
JT International S.A., Petition for Inter Partes Review of U.S. Pat. No. 8,689,805—IPR2015-01578, Ex. 1024 U.S. Pat. No. 4,771,796 to Myer, Jul. 15, 2015.
JT International S.A., Petition for Inter Partes Review of U.S. Pat. No. 8,689,805—IPR2015-01578, Ex. 1025 Halliday D., Resnick, R., Physics (Part 2) (1923), Jul. 15, 2015.
JT International S.A., Petition for Inter Partes Review of U.S. Pat. No. 8,689,805—IPR2015-01578, Ex. 1026 N.A. Fuchs, The Mechanics of Aerosols (1989), Jul. 15, 2015.
Korean Intellectual Property Office, Notice of Final Rejection for KR10-2016-7002991 with English Translation, dated Nov. 11, 2016.
Korean Intellectual Property Office, Notice of Final Rejection for KR 10-2011-7021209, with English Translation, dated Jun. 26, 2015.
Korean Intellectual Property Office, Notice of Preliminary Rejection for KR10-2011-7021209, with English Translation, dated Oct. 21, 2014.
Korean Intellectual Property Office, Notice of Preliminary Rejection for KR10-2016-7002991, with translation, dated Apr. 29, 2016.
Korean Intellectual Property Office, Notice of Second Final Rejection for KR10-2016-7002991 With English Translation, dated Mar. 13, 2017.
Korean Intellectual Property Office, Preliminary Rejection for Korean Application No. 10-2017-7036784, with English Translation, dated Apr. 9, 2018.
Nicoventures Holdings Limited, Opposition to European Patent EP2404515 (application No. EP10740882.5), Nov. 20, 2015.
Nicoventures Holdings Limited, Opposition to European Patent EP2404515 (application No. EP10740882.5), Nov. 20, 2015, Exhibit E1—Declaration of Chris Lord in respect of the public availability of the Loong Totem V9 e-cigarette, 19 pages.
Njoy, Inc et al., Defendant's Joint Invalidity Contentions, Attachment E—Claim Charts for U.S. Pat. No. 8,689,805, Aug. 7, 2014.
Njoy, Inc et al., Defendants' Joint Invalidity Contentions, Case No. CV-14-01645 etc., Aug. 7, 2014.
Njoy, Inc., Declaration of Brent K. Yamashita in Support of Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Exhibit 1 to Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Exhibit 2 to Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Exhibit 3 to Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Exhibit 4 to Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Exhibit 5 to Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Memorandum of Points and Authorities in Support of Defendants' Motion for Leave to Amend Invalidity Contentions dated Jun. 29, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., production documents VLACHOS 0000061-72; *Fontem Ventures B.V. v. Njoy, Inc.*, U.S. District Court, Central District of California, Consolidated Case No. CV 14-01645 GW (MRW) and related consolidated cases, Jun. 4, 2015.
Njoy, Inc., Reply Brief in Support of Defendants' Motion for Leave to Amend Invalidity Contentions dated Jul. 13, 2015 and filed in *Fontem Ventures B.V. v. Njoy, Inc.*, U.S. District Court, Central District of California, Consolidated Case No. CV 14-01645 GW (MRW) and related consolidated cases.
Njoy, Inc., Petition for Inter Partes Review of U.S. Pat. No. 8,689,805—IPR2015-01027, Apr. 10, 2015.
Njoy, Inc., Petition for Inter Partes Review of U.S. Pat. No. 8,689,805—IPR2015-01027, Ex. 1001 U.S. Pat. No. 8,689,805 to Hon, Apr. 10, 2015.
Njoy, Inc., Petition for Inter Partes Review of U.S. Pat. No. 8,689,805—IPR2015-01027, Ex. 1002 Declaration of Samuel David Piper, P.E., Apr. 10, 2015.
Njoy, Inc., Petition for Inter Partes Review of U.S. Pat. No. 8,689,805—IPR2015-01027, Ex. 1003 Jan. 17, 2013, Office Action, dated Apr. 10, 2015.
Njoy, Inc., Petition for Inter Partes Review of U.S. Pat. No. 8,689,805—IPR2015-01027, Ex. 1004 China Patent Application No. CN 200966824 Y to Hon, Apr. 10, 2015.
Njoy, Inc., Petition for Inter Partes Review of U.S. Pat. No. 8,689,805—IPR2015-01027, Ex. 1005 Certified English Translation of China Patent Application No. CN200966824Y to Hon, Apr. 10, 2015.
Njoy, Inc., Petition for Inter Partes Review of U.S. Pat. No. 8,689,805—IPR2015-01027, Ex. 1006 Feb. 15, 2013, Response to Office Action, dated Apr. 10, 2015.
Njoy, Inc., Petition for Inter Partes Review of U.S. Pat. No. 8,689,805—IPR2015-01027, Ex. 1007 Jun. 7, 2013, Final Office Action, dated Apr. 10, 2015.
Njoy, Inc., Petition for Inter Partes Review of U.S. Pat. No. 8,689,805—IPR2015-01027, Ex. 1008 Sep. 27, 2013, Interview Summary, dated Apr. 10, 2015.
Njoy, Inc., Petition for Inter Partes Review of U.S. Pat. No. 8,689,805—IPR2015-01027, Ex. 1009 Sep. 13, 2013, Response to Office Action, dated Apr. 10, 2015.
Njoy, Inc., Petition for Inter Partes Review of U.S. Pat. No. 8,689,805—IPR2015-01027, Ex. 1010 Sep. 13, 2013, Declaration of Lik Hon Under CFR Rule 1.132, Apr. 10, 2015.
Njoy, Inc., Petition for Inter Partes Review of U.S. Pat. No. 8,689,805—IPR2015-01027, Ex. 1011 U.S. Patent Application No. US 2009/0188490 to Hon ("Hon '490"), Apr. 10, 2015.
Njoy, Inc., Petition for Inter Partes Review of U.S. Pat. No. 8,689,805—IPR2015-01027, Ex. 1012 Dec. 23, 2013, Notice of Allowance and Examiner's Amendment, dated Apr. 10, 2015.

(56) References Cited

OTHER PUBLICATIONS

Njoy, Inc., Petition for Inter Partes Review of U.S. Pat. No. 8,689,805—IPR2015-01027, Ex. 1013 China Patent Application No. CN201018927Y to Wang, Apr. 10, 2015.
Njoy, Inc., Petition for Inter Partes Review of U.S. Pat. No. 8,689,805—IPR2015-01027, Ex. 1014 Certified English Translation of China Patent Application No. CN201018927 Y to Wang, Apr. 10, 2015.
Njoy, Inc., Petition for Inter Partes Review of U.S. Pat. No. 8,689,805—IPR2015-01027, Ex. 1015 WO 2007/131449 A1 to Hon, Apr. 10, 2015.
Njoy, Inc., Petition for Inter Partes Review of U.S. Pat. No. 8,689,805—IPR2015-01027, Ex. 1016 Certified English Translation of WO 2007/131449 A1 to Hon, Apr. 10, 2015.
Njoy, Inc., Petition for Inter Partes Review of U.S. Pat. No. 8,689,805—IPR2015-01027, Ex. 1017 U.S. Patent Application No. US 2006/0196518 to Hon, Apr. 10, 2015.
Njoy, Inc., Petition for Inter Partes Review of U.S. Pat. No. 8,689,805—IPR2015-01027, Ex. 1018 WO 2007/078273 A1 to Liu, Apr. 10, 2015.
Nu Mark LLC, Answer to Complaint and Counterclaims in *Fontem Ventures B.V.* v. *Nu Mark LLC*, 16-CV-1259, Dkt. 034, Oct. 26, 2016.
Nu Mark LLC, Answer to Complaint and Counterclaims in *Fontem Ventures B.V.* v. *Nu Mark LLC*, 16-CV-2291, Dkt. 025, Jun. 27, 2016.
Nu Mark LLC, First Amended Answer to Complaint and Counterclaims in *Fontem Ventures B.V.* v. *Nu Mark LLC*, 16-CV-2291, Dkt. 042, Jul. 28, 2016.
Nu Mark LLC, Petition for Inter Partes Review of U.S. Pat. No. 8,689,805—IPR2016-01298, Paper 1—Petition, Jun. 28, 2016.
Nu Mark LLC, Petition for Inter Partes Review of U.S. Pat. No. 8,689,805—IPR2016-01298, Ex.1001 U.S. Pat. No. 8,689,805 ("the 805 Patent"), Jun. 28, 2016.
Nu Mark LLC, Petition for Inter Partes Review of U.S. Pat. No. 8,689,805—IPR2016-01298, Ex.1002 File History for U.S. Pat. No. 8,689,805 (excerpts), Jun. 28, 2016.
Nu Mark LLC, Petition for Inter Partes Review of U.S. Pat. No. 8,689,805—IPR2016-01298, Ex.1003 Declaration of Dr. John M. Collins ("Collins Decl."), Jun. 28, 2016.
Nu Mark LLC, Petition for Inter Partes Review of U.S. Pat. No. 8,689,805—IPR2016-01298, Ex.1004 Chinese Utility Model Publication No. CN 201018927Y ("Wang"), Jun. 28, 2016.
Nu Mark LLC, Petition for Inter Partes Review of U.S. Pat. No. 8,689,805—IPR2016-01298, Ex.1005 Certified Translation of CN 201018927Y, Jun. 28, 2016.
Nu Mark LLC, Petition for Inter Partes Review of U.S. Pat. No. 8,689,805—IPR2016-01298, Ex.1006 WIPO Publication No. WO 2007/078273 ("Liu"), Jun. 28, 2016.
Nu Mark LLC, Petition for Inter Partes Review of U.S. Pat. No. 8,689,805—IPR2016-01298, Ex.1007 WIPO Publication No. WO 2007/131449 ("Hon"), Jun. 28, 2016.
Nu Mark LLC, Petition for Inter Partes Review of U.S. Pat. No. 8,689,805—IPR2016-01298, Ex.1008 Certified Translation of WIPO Publication No. WO 2007/131449, Jun. 28, 2016.
Nu Mark LLC, Petition for Inter Partes Review of U.S. Pat. No. 8,689,805—IPR2016-01298, Ex.1009 Chinese Utility Model Publication No. CN 201085044Y ("Fang"), Jun. 28, 2016.
Nu Mark LLC, Petition for Inter Partes Review of U.S. Pat. No. 8,689,805—IPR2016-01298, Ex.1010 Certified Translation of CN 201085044Y, Jun. 28, 2016.
Nu Mark LLC, Petition for Inter Partes Review of U.S. Pat. No. 8,689,805—IPR2016-01298, Ex.1011 U.S. Patent Application No. 2006/0093977 A1 ("Pellizzari I"), Jun. 28, 2016.
Nu Mark LLC, Petition for Inter Partes Review of U.S. Pat. No. 8,689,805—IPR2016-01298, Ex.1012 U.S. Pat. No. 7,059,307 ("Pellizzari II"), Jun. 28, 2016.
Nu Mark LLC, Petition for Inter Partes Review of U.S. Pat. No. 8,689,805—IPR2016-01298, Ex.1013 U.S. Pat. No. 2,057,353 ("Whittemore"), Jun. 28, 2016.
Nu Mark LLC, Petition for Inter Partes Review of U.S. Pat. No. 8,689,805—IPR2016-01298, Ex.1014 U.S. Pat. No. 5,894,841 ("Voges"), Jun. 28, 2016.
Nu Mark LLC, Petition for Inter Partes Review of U.S. Pat. No. 8,689,805—IPR2016-01298, Ex.1015 U.S. Pat. No. 6,155,268 ("Takeuchi"), Jun. 28, 2016.
Nu Mark LLC, Petition for Inter Partes Review of U.S. Pat. No. 8,689,805—IPR2016-01298, Ex.1016 U.S. Pat. No. 5,743,251 ("Howell"), Jun. 28, 2016.
Nu Mark LLC, Petition for Inter Partes Review of U.S. Pat. No. 8,689,805—IPR2016-01298, Ex.1017 U.S. Pat. No. 6,501,052 ("Cox"), Jun. 28, 2016.
Nu Mark LLC, Petition for Inter Partes Review of U.S. Pat. No. 8,689,805—IPR2016-01298, Ex.1018 U.S. Pat. No. 6,491,233 ("Nichols"), Jun. 28, 2016.
Nu Mark LLC, Petition for Inter Partes Review of U.S. Pat. No. 9,320,300—IPR2016-01773, Paper 1—Petition, Sep. 9, 2016.
Nu Mark LLC, Petition for Inter Partes Review of U.S. Pat. No. 9,320,300—IPR2016-01773, Exhibit 1001—U.S. Pat. No. 9,230,300, Sep. 9, 2016.
Nu Mark LLC, Petition for Inter Partes Review of U.S. Pat. No. 9,320,300—IPR2016-01773, Exhibit 1002—U.S. Pat. No. 9,230,300 FH Excerpts, Sep. 9, 2016.
Nu Mark LLC, Petition for Inter Partes Review of U.S. Pat. No. 9,320,300—IPR2016-01773, Exhibit 1003—Declaration of Dr. John M. Collins, Sep. 9, 2016.
Nu Mark LLC, Petition for Inter Partes Review of U.S. Pat. No. 9,320,300—IPR2016-01773, Exhibit 1004—CN 201018927, Sep. 9, 2016.
Nu Mark LLC, Petition for Inter Partes Review of U.S. Pat. No. 9,320,300—IPR2016-01773, Exhibit 1005—CN 201018927 English Translation, Sep. 9, 2016.
Nu Mark LLC, Petition for Inter Partes Review of U.S. Pat. No. 9,320,300—IPR2016-01773, Exhibit 1006—WO/2007/078273A1, Sep. 9, 2016.
Nu Mark LLC, Petition for Inter Partes Review of U.S. Pat. No. 9,320,300—IPR2016-01773, Exhibit 1007—U.S. Pat. No. 8,689,805, Sep. 9, 2016.
Nu Mark LLC, Petition for Inter Partes Review of U.S. Pat. No. 9,320,300—IPR2016-01773, Exhibit 1008—U.S. Pat. No. 7,997,280, Sep. 9, 2016.
Nu Mark LLC, Petition for Inter Partes Review of U.S. Pat. No. 9,320,300—IPR2016-01773, Exhibit 1009—U.S. Pat. No. 4,219,032, Sep. 9, 2016.
Nu Mark LLC, Petition for Inter Partes Review of U.S. Pat. No. 9,320,300—IPR2016-01773, Exhibit 1010—U.S. 2006/0016453, Sep. 9, 2016.
Nu Mark LLC, Petition for Inter Partes Review of U.S. Pat. No. 9,320,300—IPR2016-01773, Exhibit 1011—U.S. Pat. No. 7,445,007, Sep. 9, 2016.
Nu Mark LLC, Petition for Inter Partes Review of U.S. Pat. No. 9,320,300—IPR2016-01773, Exhibit 1012—Thermodynamics (Fifth Edition), Sep. 9, 2016.
Nu Mark LLC, Petition for Inter Partes Review of U.S. Pat. No. 9,320,300—IPR2016-01773, Exhibit 1013—U.S. Pat. No. 5,894,841, Sep. 9, 2016.
Nu Mark LLC, Petition for Inter Partes Review of U.S. Pat. No. 9,320,300—IPR2016-01773, Exhibit 1014—U.S. Pat. No. 6,155,268, Sep. 9, 2016.
Nu Mark LLC, Petition for Inter Partes Review of U.S. Pat. No. 9,320,300—IPR2016-01773, Exhibit 1015—U.S. Pat. No. 2,057,353, Sep. 9, 2016.
Nu Mark LLC, Petition for Inter Partes Review of U.S. Pat. No. 9,320,300—IPR2016-01773, Exhibit 1016—U.S. 2011/0120482, Sep. 9, 2016.
Nu Mark LLC, Petition for Inter Partes Review of U.S. Pat. No. 9,320,300—IPR2016-01773, Exhibit 1017—U.S. Pat. No. 6,938,986, Sep. 9, 2016.
Nu Mark LLC, Petition for Inter Partes Review of U.S. Pat. No. 9,320,300—IPR2016-01773, Exhibit 1018—U.S. 2007/0030306A1, Sep. 9, 2016.
Pan, Fenglin, Request for Invalidation of CN200920001296.3, with English Translation, Jun. 20, 2013.

(56) References Cited

OTHER PUBLICATIONS

Philip Morris Products S.A., Opposition to a European Patent EP2404515 (application No. EP10740882.5), May 6, 2016, 32 pgs.
Philip Morris Products S.A., Response filed in Opposition of European Patent No. 2404515B1, Jan. 19, 2018, 33 pgs.
State Intellectual Property Office China, Decision of Patent Invalidation Petition, CN200920001296.3, with English Translation, Sep. 19, 2014.
State Intellectual Property Office China, Decision of Rejection for CN201080016105.6, dated Jul. 28, 2015.
State Intellectual Property Office China, International Search Report for PCT/CN10/000125, dated Apr. 1, 2010.
State Intellectual Property Office China, Office Action for CN201080016105.6, with English Translation, dated Dec. 27, 2012.
State Intellectual Property Office China, Office Action for CN201080016105.6, with English Translation, dated Aug. 30, 2013.
State Intellectual Property Office China, Office Action for CN201080016105.6, with English Translation, dated Mar. 13, 2014.
State Intellectual Property Office China, Office Action for CN201080016105.6, with English Translation, dated Mar. 30, 2015.
State Intellectual Property Office PRC China, Notification of Acceptance of Request for Invalidation for CN200920001296.3 by Petitioner Shanghai Keyao Industrial Co., Ltd., Mar. 3, 2016 (English Translation).
State Intellectual Property Office PRC China, Notification of Acceptance of Request for Invalidation for CN201080016105.6 with English Summary, Mar. 28, 2017.
State Intellectual Property Office PRC China, Patent Reexamination Board, (PRB), Decision of Invalidation request filed by Shanghai Keyao Industrial Co., Ltd for CN 200920001296.3, Oct. 10, 2016 (English Translation).
State Intellectual Property PRC China, Invalidation Decision issued regarding Petition of Fang Xiao for Invalidation of CN Patent No. ZL201080016105.6, with English translation, Feb. 8, 2018, 46 pgs.

U.S. District Court for the Central District of California, *Fontem Ventures B.V.* v. *Njoy, Inc.*, Case 2:14-cv-1645-Gw-Mrw, Dkt. No. 65, Rulings on Claims Construction, Jan. 29, 2015, 28 Pages.
U.S. District Court for the Central District of California, *Fontem Ventures B.V.* v. *Njoy, Inc.*, Case No. CV 14/1645-GW(MRWx), Dkt. No. 133, Order regarding Markman Hearing/Claim Construction, May 7, 2015, 16 pages.
USPTO PTAB, IPR2014-01529 Paper 6, Decision Instituting Inter Partes Review of U.S. Pat. No. 8,689,805, Mar. 12, 2015.
USPTO PTAB, IPR2015-01027 Paper 10, Decision Instituting Inter Partes Review of U.S. Pat. No. 8,689,805, Jun. 5, 2015.
U.S. Appl. No. 13/208,257, Nonfinal Office Action, dated Feb. 4, 2013.
U.S. Appl. No. 13/426,817, Nonfinal Office Action, dated Jan. 17, 2013.
U.S. Appl. No. 13/426,817, Final Office Action, dated Jun. 7, 2013.
U.S. Appl. No. 14/307,663, Nonfinal Office Action, dated Nov. 6, 2014.
U.S. Appl. No. 14/307,663, Notice of Allowance, dated Mar. 22, 2016.
U.S. Appl. No. 15/091,017, Nonfinal Office Action, dated May 19, 2017.
U.S. Appl. No. 15/091,017, Final Office Action, dated Dec. 13, 2017.
U.S. Appl. No. 15/091,017, Notice of Allowance, dated Jul. 12, 2018.
U.S. Appl. No. 15/446,753, Nonfinal Office Action, dated Jun. 14, 2017.
U.S. Appl. No. 15/446,753, Final Office Action, dated Dec. 21, 2017.
U.S. Appl. No. 15/446,753, Interview Summary with Corrected Notice of References Cited, dated Mar. 16, 2018.
U.S. Appl. No. 15/466,753, Advisory Action, dated May 3, 2018.
IP Office Japan, Decision of Rejection for Application No. 2017-093905 with English translation, dated Nov. 5, 2019, 6 pgs.

* cited by examiner

ELECTRONIC CIGARETTE

CROSS-REFERENCE TO RELATED APPLICATIONS

This application is a continuation of U.S. application Ser. No. 15/091,017, filed Apr. 5, 2016 and now, which is a continuation of U.S. application Ser. No. 14/307,663, filed Jun. 18, 2014, now U.S. Pat. No. 9,320,300, which is a continuation of U.S. application Ser. No. 13/208,257 filed Aug. 11, 2011 and now abandoned, which is a Continuation of International Application No. PCT/CN2010/000125, filed Jan. 28, 2010, which claims priority to Chinese Patent Application No. 200920001296.3, filed Feb. 11, 2009. Each of these applications is incorporated herein by reference.

BACKGROUND OF THE INVENTION

As a cigarette substitute, atomizing electronic cigarettes have occupied a large percentage of the market for smoking substitute products. The improvement of atomizing electronic cigarette technology is a prerequisite for widespread application and acceptance of electronic cigarettes.

At present, the existing atomizing electronic cigarettes still have many problems and shortcomings, for example, poor atomization, large liquid drops in the final atomized smoke, nonuniform smoke caused by different sizes of liquid drops, too much moisture in the smoke, poor mouthfeel, etc. In some conditions, the smoke is at a high temperature because of insufficient cool-down and will cause discomfort.

The above problems cause significant differences between real cigarettes and electronic cigarettes for smokers, which is not conducive for smokers to select electronic cigarettes in place of real ones.

SUMMARY OF THE INVENTION

In order to overcome various shortcomings in the prior art, some embodiments of the invention provide an improved atomizing electronic cigarette having a liquid permeating component in an atomizer that is sleeved on an electric heater. Cigarette liquid stored in a liquid storage component permeates into the liquid permeating component. The electric heater interacts with the liquid permeating component, such that the cigarette liquid is atomized with smaller and more uniform droplets. In another aspect, by communicating through holes and channels provided and arranged in the electric heater and the liquid storage component, the atomized large drops can adhere to the liquid storage component under the pressure of airflow, such that the inhaled smoke is more similar to the feel a real cigarettes to more suitable meet the taste of smoker.

An embodiment of the invention is an improved atomizing electronic cigarette comprising a power supply unit, a sensor, an atomizing core component and a liquid storage component, within a housing. An air inlet is arranged on the housing. One end of the housing is provided with an air suction port. The atomizing core component comprises an electric heater that can atomize liquid from the liquid storage component.

The liquid storage component can be internally provided with a hollow channel, a through-hole channel, an annular channel or a cross section of sparse mesh channels or combinations thereof, through which gas flows.

The atomizing core component can further comprise a liquid conduction or transportation component in contact with the liquid permeating component and the liquid storage component.

The liquid conduction or transportation component can be sleeved on the liquid permeating component, and include a conduction part that extends from one end of the liquid conduction component in the radial direction to contact with the liquid storage component.

The sensor can be an air pressure sensor or air flow sensor. The housing can comprise a first housing and a second housing, the power device and the sensor are located in the first housing, the atomizing core component and the liquid storage component are located in the second housing, and the auxiliary air inlet is arranged in an area of the first housing and/or the second housing.

The electric heater can be formed by spirally winding electric heating wires or made up of electric heating film arranged on the inner surface of the liquid permeating component, and the electric heater formed by spirally winding or electric heating film on the inner surface of the liquid permeating component can be hollow to form the through hole.

Atomized large drops can be absorbed at, or adhere to, the liquid storage component under the pressure of airflow, a common problem in the prior art where vapor having large particles is passed directly to the user. Thus current embodiments produce inhaled smoke that more closely meets the taste of smoker.

The cigarette liquid can permeate and conduct more sufficiently and rapidly, to more efficiently produce vapor or atomized smoke. In addition, the structure is simple and saves space, such that the volume of the whole atomizing electronic cigarette can be smaller.

In another embodiment of the invention, the electronic cigarette is designed to be detachable and changeable, such that change of components can be simply achieved by detaching and reassembling the first and second housings. Such an electronic cigarette is more convenient to carry as it is also more portable.

DETAILED DESCRIPTION OF THE INVENTION

Figure 1:
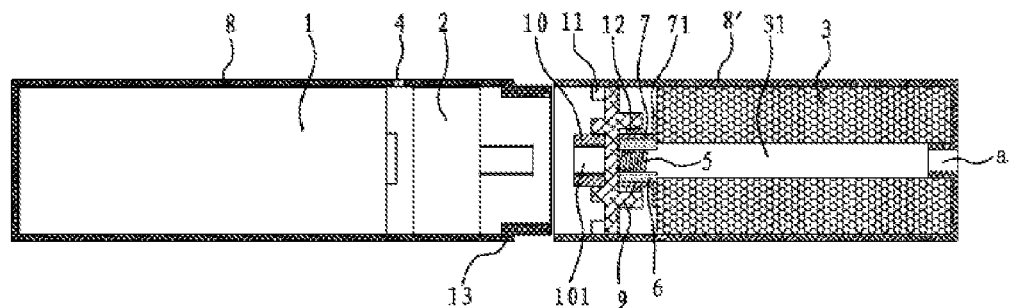
FIG. 1 is a side sectional view of an electronic cigarette according to the invention, showing the first housing separate from the second housing.

The invention will be described in detail below in conjunction with the drawings.

As shown in FIGS. 1 to 5, the invention provides an improved atomizing electronic cigarette, comprising a power device 1, a sensor 2, an atomizing core component and a liquid storage component 3, further comprising a housing containing the above components. An air inlet 4 is arranged on an area of the housing close to the sensor 2. The atomizing core component comprises an electric heater 5 and a liquid permeating component 6 sleeved on the electric heater 5. The electric heater 5 is a hollow structure and has a through hole 51 through which gas flows. The liquid storage component 3 internally has a channel 31 through which the gas flows. The channel can be a hollow channel, a through-hole channel, an annular channel or a channel with mesh cross section or combinations thereof. The purpose is to make the atomized gas that passes through the channel contact with the liquid storage core of the liquid storage component, and to make the liquid storage component 3 coordinate with the liquid permeating component 6 to permeate cigarette liquid to the liquid permeating component 6. In addition, the sensor 2 communicates with the through hole 51 and the channel 31 and forms an airflow loop with the auxiliary air inlet 4.

Figure 2:
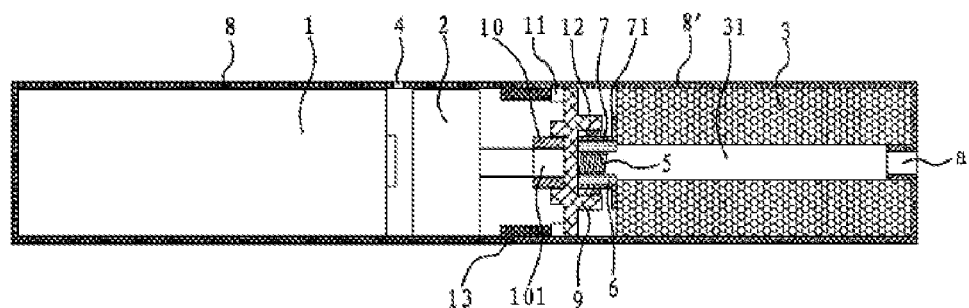
FIG. 2 is a side sectional view of an electronic cigarette according to the invention, showing the first housing connected to the second housing.
Figure 3:
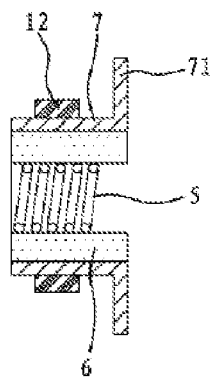
FIG. 3 is a side sectional view of an atomizing core component in an electronic cigarette according to the invention.
Figure 4:
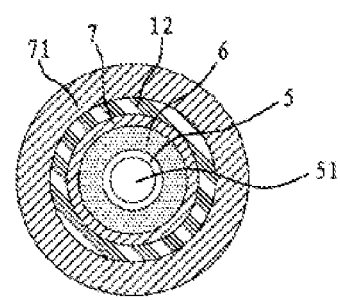
FIG. 4 is a top view of an atomizing core component in an electronic cigarette according to the invention.
Figure 5:
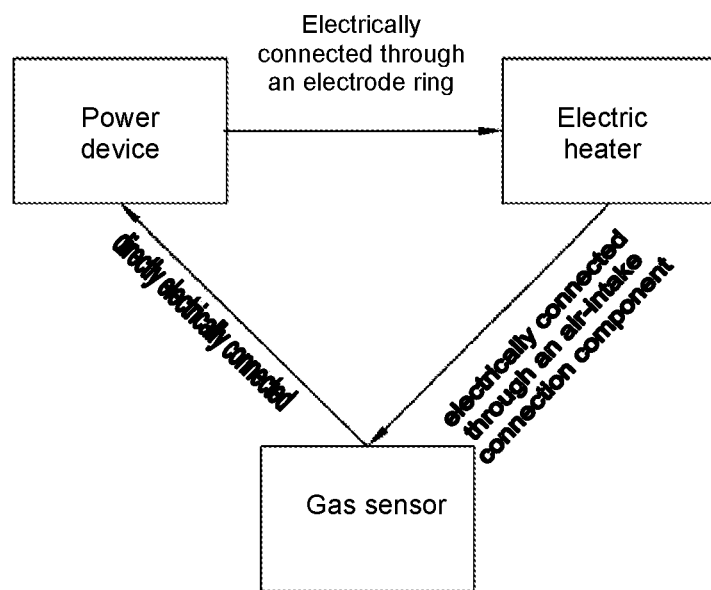
FIG. 5 is an electrical connection block diagram for forming a closed loop among components of an electronic cigarette according to the invention.

In the embodiment, as shown in FIGS. 1 to 3, the atomizing core component further comprises a liquid conduction component 7 that is contacted with the liquid permeating component 6 and with the liquid storage component 3. The liquid conduction component 7 is sleeved on the liquid permeating component 6, with a conduction part 71 that extends from one end of the liquid conduction component in the radial direction, and is contacted with the liquid storage component 3. As a result, cigarette liquid on the liquid storage component 3 is absorbed and permeated to the liquid permeating component. To make the liquid conduction component 7 mate with the liquid permeating component 6 more tightly to improve the liquid conductivity, a fastening sleeve 12 can be sleeved on the liquid conduction component 7.

The sensor 2 can be an air pressure sensor or airflow sensor. In the embodiment, an airflow sensor is used. The housing comprises a first housing 8 and a second housing 8', the power supply unit 1 and the sensor 2 which are located in the first housing 8. The atomizing core component and the liquid storage component 3 are located in the second housing 8'. The auxiliary air inlet 4 is arranged in an area of the first housing 8 and/or the second housing 8' close to the sensor 2. In the embodiment, the auxiliary air inlet 4 is arranged on the first housing 8 and located in an area close to the sensor 2. The power supply unit 1 is a battery that can be a rechargeable battery or disposable battery.

A bracket 9 is arranged in the second housing 8'. The atomizing core component is fixed on the bracket 9, and the electric heater 5 is connected with the power device 1 and the sensor 2 and starts to heat or stops heating according to the flow situation detected by the sensor 2. An air-intake connection component 10 and an electrode ring 11 are arranged on the bracket 9. The air-intake connection component 10 and the electrode ring 11 are electrically connected with two leads of the electric heater 5, respectively. The air-intake connection component 10 achieves an electrical connection through connection with the sensor 2. The electrode ring 11 is electrically connected with the power device 1 through the connection of the air-intake connection component 10 and the sensor 2. The function of the sensor is to switch on or off the whole circuit according to the gas flow. When user inhales, gas inside the electronic cigarette flows. At this time, the sensor switches the circuit on to start the electric heater 5 to heat. When the user stops inhaling, gas stops flowing, and the sensor switches the circuit off to make the electric heater 5 stop heating. An electrode ring post 13 corresponding to the electrode ring 10 is arranged at the opening of the first housing 8. A contact part 131 extends from the electrode ring post 13 in the axial direction. The electrode ring post 13 is connected with the power device 1.

When the first housing 8 and the second housing 8' are connected, the contact part 131 is inserted into the second housing 8' and contacted with the electrode ring 11.

In this embodiment, the first housing 8 and the second housing 8' are connected through the connection of the air-intake connection component 10 and the sensor 2, and the air-intake connection component 10 and the sensor 2 are connected by means of splicing or plugging, threads, or clamping. Through such a detachable and changeable split structure, the change of components can be simply achieved by detaching and reassembling the first housing 8 and the second housing 8', such that it is convenient to carry and use the electronic cigarette. This embodiment discloses a connection structure by means of threads.

As shown in FIG. 1, the air-intake connection component 10 also has an air vent 101. The sensor 2 communicates with the air vent 101, the through hole 51 and the channel 31 and forms an airflow path with the auxiliary air inlet 4. An air suction port 32 is arranged on the second housing 8', and the sensor 2 communicates with the air vent 101, the through hole 51, the channel 31 and the air suction port 32 and forms an airflow path with the auxiliary air inlet 4.

The liquid storage component 3 is made of liquid storage core materials such as micro-porous ceramic, foamed ceramic, natural fiber, artificial fiber or foam metal material. The liquid permeating component 6 is made of ceramic fiber, quartz fiber, glass fiber, aramid fiber, common fiber, paper, fabric or non-woven fabric material. The thickness of the liquid permeating component 6 is from 0.5 to 5 mm. The electric heater 5 is formed by spirally winding electric heating wires, which forms the through hole 51. The diameter of the through hole 51 can be from 0.5 to 4 mm. In this embodiment, the thickness of the liquid permeating component 6 is 1 mm, and the diameter of the through hole 51 is 1 mm.

The liquid permeating component 6 in the atomizing core component is directly sleeved on the electric heater 5. Cigarette liquid in the liquid storage component 3 is conducted and permeated to the liquid permeating component 6 by the liquid conduction component 7. The thickness of the liquid permeating component 6 is 1 mm. As a result, the permeated cigarette liquid can be completely vaporized by the electric heater 5 more easily. When the user inhales, as the sensor 2 communicates with the air vent 101, the through hole 51, the channel 31 and the air suction port 32 and forms an airflow path with the auxiliary air inlet 4. When gas flow is generated inside the electronic cigarette, the sensor 3 switches the circuit on, the electric heater 5 starts to heat to make the cigarette liquid in the liquid permeating component 6 be vaporized after reaching the boiling point. At the same time, because the through hole 51 and the channel 31 of the electric heater 5 and the liquid storage component 3 are in communication, vapor generated during atomizing process can be further cooled under the push of airflow and finally inhaled into the user's mouth through the air suction port 32.

Figure 6:
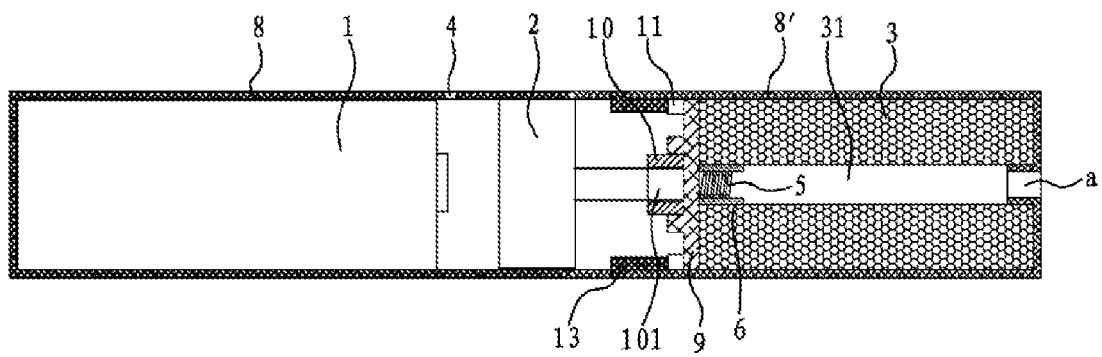
FIG. 6 is a side cutaway view of an electronic cigarette according to another embodiment of the invention.

In another preferred embodiment of the invention, as shown in FIG. 6, the liquid permeating component 6 is contacted with the liquid storage component 3. The atomizing core component is sleeved in the channel 31 of the liquid storage component 3, and the peripheral surface of the liquid permeating component 6 is mated with the inner wall of the channel 31.

The liquid storage component 3 can be made of micro-porous ceramic, foamed ceramic, natural fiber, artificial fiber or foam metal material. The liquid permeating component 6 can be made of ceramic fiber, quartz fiber, glass fiber, aramid fiber, common fiber, paper, fabric or non-woven fabric material. The thickness of the liquid permeating component 6 ranks from 0.5 to 5 mm. The electric heater 5 is formed by spirally winding electric heating wires to form a through hole 51. The diameter of the through hole 51 can be from 0.5 to 4 mm. In this embodiment, the thickness of the liquid permeating component 6 is 1 mm and the diameter of the through hole 51 is 1 mm.

In this embodiment, the atomizing core component is integrally sleeved in the channel 31 of the liquid storage component 3, such that the surface of the liquid permeating component 6 is directly contacted with the inner wall of the channel 31 of the liquid storage component 3. Because the contact area is larger, the permeation and conduction of cigarette liquid is more sufficient and rapid, and the atomized smoke efficiently generated. At the same time, the structure is simple and saves space, so as to minimize the size of the atomizing electronic cigarette.

In other embodiments, an improved atomizing electronic cigarette is provided comprising a power device (1), a sensor (2), an atomizing core component and a liquid storage component (3), further comprising a housing containing the above components, an auxiliary air inlet (4) being arranged on the housing. One end of the housing is provided with an air suction port, characterized in that the atomizing core component comprises an electric heater (5), the electric heater (5) atomizes liquid in a liquid storage component (3). The liquid storage component (3) internally has a channel (31) through which the atomized gas flows, and the auxiliary air inlet (4), the sensor (2) and the suction nozzle form an airflow loop.

In other aspects the atomizing electronic cigarette can be characterized in that the atomizing core component comprises a liquid permeating component (6) that is sleeved on the electric heater (5), a channel (51) through which gas flows is arranged in the atomizing core component, and the channel (51) is made up of the structure of the electric heater (5).

In other aspects the atomizing electronic cigarette can be characterized in that the electric heater (5) of the atomizing core component is directly inserted into the channel (31) of the liquid storage component (3), and the atomized gas directly flows through the channel (31).

In other aspects the atomizing electronic cigarette is characterized in that the liquid storage component (3) is internally provided with the channel (31) which is a hollow channel, a through-hole channel, an annular channel or a channel with mesh in cross section or combinations thereof, through which gas flows.

In other aspects the atomizing electronic cigarette is characterized in that the atomizing core component further comprises a liquid conduction component (7) that is contacted with the liquid permeating component (6), and with the liquid storage component (3).

In other aspects, the atomizing electronic cigarette is characterized in that the liquid conduction component (7) is sleeved on the liquid permeating component (6), a conduction part (71) extends from one end of the liquid conduction component in the radial direction, and the conduction part (71) is contacted with the liquid storage component (3).

In other aspects, the atomizing electronic cigarette is characterized in that the sensor (2) is an air pressure sensor or airflow sensor, the housing comprises a first housing (8) and a second housing (8'), the power device (1) and the sensor (2) are located in the first housing (8), the atomizing core component and the liquid storage component (3) are located in the second housing (8'), and the auxiliary air inlet (4) is arranged in an area of the first housing (8) and/or the second housing (8') close to the sensor.

In other aspects, the atomizing electronic cigarette is characterized in that a bracket (9) is arranged in the second housing (8'), the atomizing core component is fixed on the bracket (9), and the electric heater (5) is connected with the power device (1) and the sensor (2) and starts to heat or stops heating according to the flow situation of gas through the sensor (2).

In other aspects, the atomizing electronic cigarette is characterized in that an air-intake connection component (10) and an electrode ring (11) are arranged on the bracket (9), the air-intake connection component (10) and the electrode ring (11) are electrically connected with two leads of the electric heater (5) respectively, the air-intake connection component (10) achieves electric connection through connection with the sensor (2), the electrode ring (11) is electrically connected with the power device (1) through the connection of the air-intake connection component (10) and the sensor (2), the air-intake connection component (10) also has an air vent (101), the sensor (2) communicates with the air vent (101), the through hole (51) and the channel (31) and forms an airflow path with the auxiliary air inlet (4).

In other aspects, the atomizing electronic cigarette is characterized in that the first housing (8) and the second housing (8') are connected through the connection of the air-intake connection component (10) and the sensor (2), and the air-intake connection component (10) and the sensor (2) are connected by means of splicing or plugging, threads or clamping.

In other aspects, the atomizing electronic cigarette is characterized in that an air suction port (a) is arranged on the second housing (8'), and the sensor (2) communicates with the air vent (101), the through hole (51), the channel (31) and the air suction port (a) and forms an airflow loop with the auxiliary air inlet (4).

In other aspects, the atomizing electronic cigarette is characterized in that the housing is an integrated whole, the front end of which is provided with the auxiliary air inlet (4), and the sensor (2) communicates with the air vent (101), the through hole (51), the channel (31) and the air suction port (a) and forms an airflow loop with the auxiliary air inlet (4).

In other aspects, the atomizing electronic cigarette is characterized in that the liquid permeating component (6) is contacted with the liquid storage component (3), the atomizing core component is sleeved in the channel (31) of the liquid storage component (3), and the peripheral surface of the liquid permeating component (6) is mated with the inner wall of the channel (31).

In other aspects, the atomizing electronic cigarette is characterized in that the liquid storage component (3) is made of micro-porous ceramic, foamed ceramic, natural fiber, artificial fiber or foam metal material, the liquid permeating component (6) is made of ceramic fiber, quartz fiber, glass fiber, aramid fiber, common fiber, paper, fabric or non-woven fabric material, the electric heater (5) is formed by spirally winding electric heating wires or made up of electric heating film arranged on the inner surface of the liquid permeating component, and the electric heater formed by spirally winding or electric heating film on the inner surface of the liquid permeating component is hollow to form the through hole (51).

In other aspects, the atomizing electronic cigarette is characterized in that the thickness of the liquid permeating component (6) ranks from 0.5 to 5 mm, and the diameter of the through hole (51) ranks from 0.5 to 4 mm.

In other aspects, the atomizing electronic cigarette is characterized in that zeolite particles are added in the liquid permeating component (6).

I claim:

1. An electronic cigarette, comprising:
a first housing containing a power device;
a second housing containing an atomizer and providing liquid storage containing liquid and an unobstructed channel through the liquid storage;
the atomizer in the second housing, the atomizer including a wire coil and a liquid permeating component, the liquid storage around the atomizer;
the liquid permeating component having a first axis, the liquid permeating component in contact with the wire coil along the first axis, and the liquid permeating component in contact with liquid from the liquid storage;
the unobstructed channel through the liquid storage extending from the atomizer to an outlet at an end of the second housing, the channel surrounded by the liquid storage;
an air inlet for allowing air into the second housing;
an air flow path from the air inlet through the atomizer and the channel to the outlet;
a first electrode in the first housing;
a second electrode in the second housing, the second electrode adapted to electrically connect with the first electrode when the first housing is connected to the second housing.

2. The electronic cigarette of claim 1 further comprising an air flow sensor electrically connected to the power device and positioned to sense air flow in the air flow path.

3. The electronic cigarette of claim 1 wherein the liquid permeating component is cylindrical and co-axial with the wire coil.

4. The electronic cigarette of claim 1 wherein the liquid permeating component comprises a glass material.

5. The electronic cigarette of claim 1 wherein the atomizer is supported on a bracket in the second housing and wherein the bracket is at an end of the second housing opposite from the outlet.

6. The electronic cigarette of claim 1 with the second housing connected to the first housing by plugging.

7. The electronic cigarette of claim 1 with liquid from the liquid storage moving into the liquid permeating component, and the wire coil providing heat to create a vapor.

8. The electronic cigarette of claim 1 wherein the channel extends continuously from the atomizer through the liquid storage.

9. The electronic cigarette of claim 1 wherein the liquid permeating component comprises a fibrous material.

10. The electronic cigarette of claim 1 wherein the liquid permeating component comprises ceramic.

11. The electronic cigarette of claim 1 wherein the liquid permeating component comprises quartz fiber, aramid fiber, common fiber, paper, fabric or non-wove fabric material.

12. The electronic cigarette of claim 1 wherein the atomizer is supported on a bracket in the second housing, the second electrode on the bracket, and the air inlet extending through the bracket.

13. An electronic cigarette comprising:
a housing having an air inlet and an air outlet;
a battery and an atomizer in the housing, the atomizer comprising an electric heater;
a liquid storage encircling the atomizer;
a cylindrical liquid permeating component having a longitudinal axis, and the electric heater in contact with the cylindrical liquid permeating component;
with liquid from the liquid storage permeating into the cylindrical liquid permeating component, and the electric heater heating the liquid into a vapor;
the liquid storage internally has a channel wall forming an unobstructed through-hole channel through which the vapor flows, with the vapor in contact with the channel wall;
the through-hole channel extending continuously from the atomizer through the liquid storage; and
the air inlet, the through-hole channel and the air outlet forming an airflow passageway through the housing.

14. The electronic cigarette of claim 13 wherein the housing comprises a first housing attached to a second housing, with the battery and an airflow sensor in the first housing and with the atomizer and the liquid storage in the second housing.

15. The electronic cigarette of claim 13 with a peripheral surface of the liquid permeating component mated with an inner wall of the channel.

16. The electronic cigarette of claim 13 with the liquid permeating component comprising quartz fiber, glass fiber, aramid fiber, common fiber, paper, fabric or non-woven fabric material.

17. The electronic cigarette of claim 13 wherein a first end of the electric heater and a first end of the liquid storage are in contact with a bracket in the housing.

18. The electronic cigarette of claim 13 with the liquid permeating component comprising a ceramic material.

19. The electronic cigarette of claim 13 with the electric heater comprising a wire coil.

20. The electronic cigarette of claim 13 with the electric heater comprising an electric heating film.

21. The electronic cigarette of claim 13 with the air flow passageway including a through hole in the cylindrical liquid permeating component having a diameter of 0.5 to 4 mm.

22. The electronic cigarette of claim 13 with the cylindrical liquid permeating component having a thickness of 0.5 to 5 mm.

23. An electronic cigarette, comprising:
a first housing containing a rechargeable battery, an air flow sensor and a first electrode;
a second housing attachable to the first housing, the second housing having a second electrode at a first end of the second housing, the second electrode adapted to electrically connect with the first electrode when the first housing is attached to the second housing;
the second housing providing a liquid storage containing liquid;
a wire coil within the liquid storage, at the first end of the second housing, the wire coil electrically connected to the second electrode;
an unobstructed through-hole channel through the liquid storage between the wire coil and an outlet at a second end of the second housing, with an air flow path from an air inlet at the first end of the second housing through the channel to the outlet; and
a cylindrical liquid permeating component in contact with the wire coil and in contact with liquid from the liquid storage, at least part of the cylindrical liquid permeating component coaxial with the wire coil.

24. The electronic cigarette of claim 23 wherein the liquid permeating component comprises a fibrous material.

25. The electronic cigarette of claim 23 wherein the first housing is attachable to the second housing by plugging.

\* \* \* \* \*

UNITED STATES PATENT AND TRADEMARK OFFICE
CERTIFICATE OF CORRECTION

| | | |
|---|---|---|
| PATENT NO. | : 10,588,353 B2 | Page 1 of 1 |
| APPLICATION NO. | : 15/902712 | |
| DATED | : March 17, 2020 | |
| INVENTOR(S) | : Lik Hon | |

It is certified that error appears in the above-identified patent and that said Letters Patent is hereby corrected as shown below:

On the Title Page

In Column 1, after the (*) Notice:, add -- This patent is subject to a terminal disclaimer --.

In the Specification

In Column 1, Line 7, delete "2016 and now," and insert -- 2016, --, therefor.

In the Claims

In Column 7, Line 58, in Claim 11, delete "non-wove" and insert -- non-woven --, therefor.

Signed and Sealed this
Fourth Day of July, 2023

Katherine Kelly Vidal
*Director of the United States Patent and Trademark Office*